United States Patent [19]

Reynolds

[11] Patent Number: 5,227,154
[45] Date of Patent: Jul. 13, 1993

[54] PHOSPHOPEPTIDES FOR THE TREATMENT OF DENTAL CALCULUS

[75] Inventor: Eric C. Reynolds, Balwyn North, Australia

[73] Assignee: The University of Melbourne, Australia

[21] Appl. No.: 748,344

[22] Filed: Aug. 22, 1991

[51] Int. Cl.$^5$ ..................... A61K 7/16; A61K 37/02
[52] U.S. Cl. ........................................ 424/49; 514/12; 514/13; 514/15; 514/17; 514/18; 530/324; 530/325; 530/326; 530/330; 530/352; 530/360
[58] Field of Search ............... 514/12, 13, 15, 17, 514/18; 424/49; 530/324, 325, 326, 327, 330, 352, 360

[56] References Cited

U.S. PATENT DOCUMENTS

| | | | |
|---|---|---|---|
| 4,515,772 | 5/1985 | Parran, Jr. | 424/57 |
| 4,590,077 | 5/1986 | Trop | 426/61 |
| 4,684,518 | 8/1987 | Parran, Jr. | 424/52 |
| 4,866,161 | 9/1989 | Sikes et al. | 530/324 |
| 4,868,287 | 9/1989 | Sikes et al. | 530/324 |
| 5,015,628 | 5/1991 | Reynolds | 514/12 |

FOREIGN PATENT DOCUMENTS 0391629  3/1990  European Pat. Off. .

*Primary Examiner*—Nathan M. Nutter
*Attorney, Agent, or Firm*—Andrus, Sceales, Starke & Sawall

[57] ABSTRACT

A method of inhibiting dental calculus by applying to the teeth an oral composition containing a dental calculus inhibiting amount of one or more of the phosphopeptides SEQ.ID NO:1 to SEQ.ID NO:9, especially in the form of a zinc/phosphopeptide complex or aggregate.

22 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 25
( B ) TYPE: Amino acid
( C ) STRANDEDNESS: single
( D ) TOPOLOGY: linear ( i i ) MOLECULE TYPE: Protein ( i x ) FEATURE:
( A ) NAME/KEY: Phosphoserine
( B ) LOCATION: 15
( D ) OTHER INFORMATION:
Post-translationally phosphorylated serine ( i x ) FEATURE:
( A ) NAME/KEY: Phosphoserine
( B ) LOCATION: 17
( D ) OTHER INFORMATION:
Post-translationally phosphorylated serine ( i x ) FEATURE:
( A ) NAME/KEY: Phosphoserine
( B ) LOCATION: 18
( D ) OTHER INFORMATION:
Post-translationally phosphorylated serine ( i x ) FEATURE:
( A ) NAME/KEY: Phosphoserine
( B ) LOCATION: 19
( D ) OTHER INFORMATION:
Post-translationally phosphorylated serine ( x i ) SEQUENCE DESCRIPTION: SEQ.ID NO:1:

Arg Glu Leu Glu Glu Leu Asn Val Pro Gly Glu Ile Val Glu Ser Leu
1               5                   10                  15
Ser Ser Ser Glu Glu Ser Ile Thr Arg
            20              25

( 2 ) INFORMATION FOR SEQ ID NO:2:

( i ) SEQUENCE CHARACTERISTICS:
( A ) LENGTH: 21
( B ) TYPE: Amino acid
( C ) STRANDEDNESS: single
( D ) TOPOLOGY: linear ( i i ) MOLECULE TYPE: Protein ( i x ) FEATURE:
( A ) NAME/KEY: Pyroglutamate
( B ) LOCATION: 1
( D ) OTHER INFORMATION:
A certain amount will exist in this form ( i x ) FEATURE:
( A ) NAME/KEY: Phosphoserine
( B ) LOCATION: 6
( D ) OTHER INFORMATION:
Post-translationally phosphorylated serine ( i x ) FEATURE:
( A ) NAME/KEY: Phosphoserine
( B ) LOCATION: 8
( D ) OTHER INFORMATION:
Post-translationally phosphorylated serine ( i x ) FEATURE:
( A ) NAME/KEY: Phosphoserine
( B ) LOCATION: 9

-continued (D) OTHER INFORMATION:
Post-translationally phosphorylated serine (ix) FEATURE:
(A) NAME/KEY: Phosphoserine
(B) LOCATION: 10
(D) OTHER INFORMATION:
Post-translationally phosphorylated serine (ix) FEATURE:
(A) NAME/KEY: Phosphoserine
(B) LOCATION: 17
(D) OTHER INFORMATION:
Post-translationally phosphorylated serine (xi) SEQUENCE DESCRIPTION: SEQ.ID NO:2:

Gln Met Glu Ala Glu Ser Ile Ser Ser Ser Glu Glu Ile Val Pro Asn
1               5                   10                  15
Ser Val Glu Gln Lys
            20

(2) INFORMATION FOR SEQ ID NO:3:

(i) SEQUENCE CHARACTERISTICS:
(A) LENGTH: 24
(B) TYPE: Amino acid
(C) STRANDEDNESS: single
(D) TOPOLOGY: linear (ii) MOLECULE TYPE: Protein (ix) FEATURE:
(A) NAME/KEY: Phosphoserine
(B) LOCATION: 14
(D) OTHER INFORMATION:
Post-translationally phosphorylated serine (ix) FEATURE:
(A) NAME/KEY: Phosphoserine
(B) LOCATION: 16
(D) OTHER INFORMATION:
Post-translationally phosphorylated serine (ix) FEATURE:
(A) NAME/KEY: Phosphoserine
(B) LOCATION: 17
(D) OTHER INFORMATION:
Post-translationally phosphorylated serine (ix) FEATURE:
(A) NAME/KEY: Phosphoserine
(B) LOCATION: 18
(D) OTHER INFORMATION:
Post-translationally phosphorylated serine (xi) SEQUENCE DESCRIPTION: SEQ.ID NO:3:

Glu Leu Glu Glu Leu Asn Val Pro Gly Glu Ile Val Glu Ser Leu Ser
1               5                   10                  15
Ser Ser Glu Glu Ser Ile Thr Arg
            20

(2) INFORMATION FOR SEQ ID NO:4:

(i) SEQUENCE CHARACTERISTICS:
(A) LENGTH: 25
(B) TYPE: Amino acid
(C) STRANDEDNESS: single
(D) TOPOLOGY: linear (ii) MOLECULE TYPE: Protein (ix) FEATURE:
(A) NAME/KEY: Phosphoserine
(B) LOCATION: 11
(D) OTHER INFORMATION:
Post-translationally phosphorylated serine (ix) FEATURE:
    (A) NAME/KEY: Phosphoserine
    (B) LOCATION: 12
    (D) OTHER INFORMATION:
        Post-translationally phosphorylated serine (ix) FEATURE:
    (A) NAME/KEY: Phosphoserine
    (B) LOCATION: 13
    (D) OTHER INFORMATION:
        Post-translationally phosphorylated serine (ix) FEATURE:
    (A) NAME/KEY: Phosphoserine
    (B) LOCATION: 16
    (D) OTHER INFORMATION:
        Post-translationally phosphorylated serine (xi) SEQUENCE DESCRIPTION: SEQ. ID NO:4:

Asn Ala Asn Glu Glu Glu Tyr Ser Ile Gly Ser Ser Ser Glu Glu Ser
1               5                   10                  15
Ala Glu Val Ala Thr Glu Glu Val Lys
            20                  25

(2) INFORMATION FOR SEQ ID NO:5:

(i) SEQUENCE CHARACTERISTICS:
        (A) LENGTH: 21
        (B) TYPE: Amino acid
        (C) STRANDEDNESS: single
        (D) TOPOLOGY: linear (ii) MOLECULE TYPE: Protein (ix) FEATURE:
        (A) NAME/KEY: Phosphoserine
        (B) LOCATION: 6
        (D) OTHER INFORMATION:
            Post-translationally phosphorylated serine (ix) FEATURE:
        (A) NAME/KEY: Phosphoserine
        (B) LOCATION: 8
        (D) OTHER INFORMATION:
            Post-translationally phosphorylated serine (ix) FEATURE:
        (A) NAME/KEY: Phosphoserine
        (B) LOCATION: 9
        (D) OTHER INFORMATION:
            Post-translationally phosphorylated serine (ix) FEATURE:
        (A) NAME/KEY: Phosphoserine
        (B) LOCATION: 10
        (D) OTHER INFORMATION:
            Post-translationally phosphorylated serine (ix) FEATURE:
        (A) NAME/KEY: Phosphoserine
        (B) LOCATION: 17
        (D) OTHER INFORMATION:
            Post-translationally phosphorylated serine (xi) SEQUENCE DESCRIPTION: SEQ. ID NO:5:

Gln Met Glu Ala Glu Ser Ile Ser Ser Ser Glu Glu Ile Val Pro Asp
1               5                   10                  15
Ser Val Glu Gln Lys
            20

(2) INFORMATION FOR SEQ ID NO:6:

(i) SEQUENCE CHARACTERISTICS:
        (A) LENGTH: 21
        (B) TYPE: Amino acid (C) STRANDEDNESS: single
(D) TOPOLOGY: linear (ii) MOLECULE TYPE: Protein (ix) FEATURE:
(A) NAME/KEY: Phosphoserine
(B) LOCATION: 6
(D) OTHER INFORMATION:
Post-translationally phosphorylated serine (ix) FEATURE:
(a) Name/Key: Phosphoserine
(b) Location: 8
(d) Other information:
Post-translationally phosphorylated serine (ix) FEATURE:
(a) Name/Key: Phosphoserine
(b) Location: 9
(d) Other information:
Post-translationally phosphorylated serine (ix) FEATURE:
(a) Name/Key: Phosphoserine
(b) Location: 10
(d) Other information:
Post-translationally phosphorylated serine (ix) FEATURE:
(a) Name/Key: Phosphoserine
(b) Location: 17
(d) Other information:
Post-translationally phosphorylated serine (xi) SEQUENCE DESCRIPTION: SEQ.ID NO:6:

```
Gln Met Glu Ala Glu Ser Ile Ser Ser Ser Glu Glu Ile Val Pro Asp
 1               5                  10                  15
Ser Val Glu Glu Lys
            20
```

(2) INFORMATION FOR SEQ ID NO:7:

(i) SEQUENCE CHARACTERISTICS:
(A) LENGTH: 20
(B) TYPE: Amino acid
(C) STRANDEDNESS: single
(D) TOPOLOGY: linear (ii) MOLECULE TYPE: Protein (ix) FEATURE:
(a) Name/Key: Phosphoserine
(b) Location: 7
(d) Other information:
Post-translationally phosphorylated serine (ix) FEATURE:
(a) Name/Key: Phosphoserine
(b) Location: 8
(d) Other information:
Post-translationally phosphorylated serine (ix) FEATURE:
(a) Name/Key: Phosphoserine
(b) Location: 9
(d) Other information:
Post-translationally phosphorylated serine (ix) FEATURE:
(a) Name/Key: Phosphoserine
(b) Location: 15
(d) Other information:
Post-translationally phosphorylated serine (xi) SEQUENCE DESCRIPTION: SEQ.ID NO:7:

```
Asn Thr Met Glu His Val Ser Ser Ser Glu Glu Ser Ile Ile Ser Gln
 1               5                  10                  15
```

```
Glu Thr Tyr Lys
            20
```

( 2 ) INFORMATION FOR SEQ ID NO:8:

( i ) SEQUENCE CHARACTERISTICS:
        ( A ) LENGTH: 21
        ( B ) TYPE: Amino acid
        ( C ) STRANDEDNESS: single
        ( D ) TOPOLOGY: linear ( i i ) MOLECULE TYPE: Protein ( i x ) FEATURE:
        ( a ) Name/Key: Phosphoserine
        ( b ) Location: 8
        ( d ) Other information:
            Post-translationally phosphorylated serine ( i x ) FEATURE:
        ( a ) Name/Key: Phosphoserine
        ( b ) Location: 9
        ( d ) Other information:
            Post-translationally phosphorylated serine ( i x ) FEATURE:
        ( a ) Name/Key: Phosphoserine
        ( b ) Location: 10
        ( d ) Other information:
            Post-translationally phosphorylated serine ( i x ) FEATURE:
        ( a ) Name/Key: Phosphoserine
        ( b ) Location: 16
        ( d ) Other information:
            Post-translationally phosphorylated serine ( x i ) SEQUENCE DESCRIPTION: SEQ.ID NO:8:

```
Lys Asn Thr Met Glu His Val Ser Ser Ser Glu Glu Ser Ile Ile Ser
1               5                   10                      15
Gln Glu Thr Tyr Lys
            20
```

( 2 ) INFORMATION FOR SEQ ID NO:9:

( i ) SEQUENCE CHARACTERISTICS:
        ( A ) LENGTH: 37
        ( B ) TYPE: Amino acid
        ( C ) STRANDEDNESS: single
        ( D ) TOPOLOGY: linear ( i i ) MOLECULE TYPE: Protein ( i x ) FEATURE:
        ( A ) NAME/KEY: Phosphoserine
        ( B ) LOCATION: 4
        ( D ) OTHER INFORMATION:
            Post-translationally phosphorylated serine ( i x ) FEATURE:
        ( A ) NAME/KEY: Phosphoserine
        ( B ) LOCATION: 6
        ( D ) OTHER INFORMATION:
            Post-translationally phosphorylated serine ( i x ) FEATURE:
        ( A ) NAME/KEY: Phosphoserine
        ( B ) LOCATION: 22
        ( D ) OTHER INFORMATION:
            Post-translationally phosphorylated serine ( i x ) FEATURE:
        ( A ) NAME/KEY: Phosphoserine
        ( B ) LOCATION: 24
        ( D ) OTHER INFORMATION:
            Post-translationally phosphorylated serine ( i x ) FEATURE:
  ( A ) NAME/KEY: Phosphoserine
  ( B ) LOCATION: 25
  ( D ) OTHER INFORMATION:
    Post-translationally phosphorylated serine ( i x ) FEATURE:
  ( A ) NAME/KEY: Phosphoserine
  ( B ) LOCATION: 26
  ( D ) OTHER INFORMATION:
    Post-translationally phosphorylated serine ( i x ) FEATURE:
  ( A ) NAME/KEY: Phosphoserine
  ( B ) LOCATION: 33
  ( D ) OTHER INFORMATION:
    Post-translationally phosphorylated serine ( x i ) SEQUENCE DESCRIPTION: SEQ.ID NO:9:

Asp Ile Gly Ser Glu Ser Thr Glu Asp Gln Ala Met Glu Asp Ile Lys
1                5                  10                 15
Gln Met Glu Ala Glu Ser Ile Ser Ser Glu Glu Ile Val Pro Asn
           20              25                  30
Ser Val Glu Gln Lys
         35

PHOSPHOPEPTIDES FOR THE TREATMENT OF DENTAL CALCULUS

FIELD OF THE INVENTION

The invention relates to a method of controlling and preventing dental calculus by contacting the teeth with an oral composition containing specific casein phosphopeptides.

BACKGROUND AND RELATED ART

Dental calculus is a mineralised deposit that forms on the surface of teeth. The mineralised deposit is largely crystals of calcium phosphate in various forms, in particular hydroxyapatite. It is desirable to prevent the formation of dental calculus by inhibition or retardation of hydroxyapatite crystal growth and also by inhibition of the transformation of more acidic forms of calcium phosphate (e.g. brushite) or amorphous calcium phosphate into hydroxyapatite.

Parran Jr. et al have specified the use of soluble inorganic alkalimetal pyrophosphates as anti-calculus agents in oral compositions. Reference is made to U.S. Pat. No. 4,515,772; U.S. Pat. No. 4,590,077 and U.S. Pat. No. 4,684,518.

In U.S. Pat. No. 4,534,881 Sikes et al disclose synthetically derived amino acid polymers for the inhibition or retardation of inorganic scaling where the synthetic polymers may contain phosphorylated amino acids. Further, in U.S. Pat. Nos. 4,866,161 and 4,868,287 to Sikes et al. have disclosed the use of synthetic polyamino acids for the control of dental calculus where the anionic amino acids are clustered at one end of the polypeptide with non-polar residues clustered at the other. The anionic amino acids are independently selected from phosphoserine, phosphohomoserine, phosphotyrosine, phosphothreonine, glutamate and aspartate. In European Patent Application 0,391,629, Sikes has disclosed synthetic polypeptides having a formula poly$(X)_m(Y)_n$ where X is independently aspartate, glutamate, glutamine, asparagine or phosphoserine; each Y independently is a phosphorylated amino acid such as phosphoserine, phosphohomoserine, phosphotyrosine and phosphothreonine; m is 2 to 150; n is 1 to 3 and n+m is greater than or equal to 5.

SUMMARY OF INVENTION

The polypeptides taught in all of Sikes et al specifications must be synthesized and are composed of a small number of different amino acids in a specific sequence. In the present invention specific casein phosphopeptides, which differ in amino acid composition and sequence to the synthetic polypeptides of Sikes, are shown to have anti-calculus potential. These phosphopeptides have been described as anti-caries and anti-gingivitis agents in U.S. Pat. No. 5,015,628 to Reynolds and are referred to for convenience in the present specification as casein phosphopeptides (CPP).

The present invention includes to a method of controlling dental calculus by treating the teeth with an oral composition which comprises specific casein phosphopeptides and/or salts thereof. The specific casein phosphopeptides contain 5 to 40 amino acyl residues and include the sequence -Ser(P)-Ser(P)-Ser(P)-Glu-Glu where Ser(P) is phosphoserine and Glu is glutamate. Preferably they contain the sequence-Glu-Ser(P)-Ile/Leu-Ser(P)-Ser(P)-Ser(P)-Glu-Glu-where Ile is isoleucine and Leu is leucine. The casein phosphopeptides (CPP) are present in the oral composition in an amount to affect dental calculus formation.

The present invention also encompasses an oral composition in the form of a liquid dentifrice, mouthwash, toothpaste, lozenge, tablet, foodstuff or beverage or other pharmaceutically acceptable vehicle suitable for use in controlling dental calculus. These compositions may also contain an effective amount of phosphatase inhibitor (e.g. fluoride or vinyl ether maleic acid polymers) or metal ion activators (e.g. Zn(II) and Al(III)).

DETAILED DESCRIPTION OF THE INVENTION

Essential in the method for controlling dental calculus according to the present invention is the use of the specific casein phosphopeptides and/or salts thereof. The specific casein phosphopeptides contain from 5 to 40 amino acids including the sequence -Ser(P)-Ser(P)-Ser(P)-Glu-Glu- where Ser(P) is phosphoserine and Glu is glutamate. Preferred casein phosphopeptides are those that contain the sequence of amino acyl residues -Glu-Ser(P)-Ile/Leu-Ser(P)-Ser(P)-Ser(P)-Glu-Glu- where Ile is isoleucine and Leu is leucine.

A mixture of casein phosphopeptides (CPP) and/or their salts may be used in the method of the present invention. In this instance it is preferred that those containing the sequence -Glu-Ser(P)-Ile/Leu-Ser(P)-Ser(P)-Ser(P)-Glu-Glu-above predominate. The casein phosphopeptides or mixtures of CPP are preferably substantially pure at least to the extent of not containing unpalatable impurities. The casein phosphopeptides identified as SEQ.ID NO:1, SEQ.ID NO:2, SEQ.ID NO:3, SEQ.ID NO:4, SEQ.ID NO:5, SEQ.ID NO:6, SEQ.ID NO:7, SEQ.ID NO:8, SEQ.ID NO:9 in the "Sequence Listing" herein below have been found to be particularly useful in the compositions of the present invention.

The preferred casein phosphopeptides can be simply extracted from a casein digest, such digestion maybe chemical or enzymatic with proteolytic enzymes. It is preferred to digest casein with a proteolytic enzyme for example trypsin, chyotrypsin, pepsin, papain, thermolysin or pronase. Trypsin is the preferred enzyme. The digested casein can then be fractionated into phosphopeptides, containing the sequence -Ser(P)-Ser(P)-Ser(P)-Glu-Glu- and other phosphorylated and non-phosphorylated peptides. The preferred casein phosphopeptides can be purified using the selective precipitation method described in U.S. Pat. No. 5,015,628 as a calcium salt. Alternatively, instead of using $CaCl_2$ to aggregate the preferred phosphopeptides other divalent or trivalent metal ions (e.g. $ZnSO_4$) can be used to form a CPP/metal ion complex or aggregate (e.g. ZnCPP) which can then be selectively precipitated by ethanol. The sodium salt of the peptides can be formed by ion exchange of the calcium or zinc salts or alternatively by anion exchange chromatography as described in our U.S. Pat. No. 5,015,628. Ultrafiltration maybe used to separate the CaCPP or ZnCPP complexes from the remainder of the non-active casein peptides as described below. The CPP salts can be converted by ultrafiltration to sodium salts again as described below.

Sodium caseinate was prepared by acidifying milk with 0.1M HCl to pH 4.7 and neutralising the precipitate with NaOH to pH 7.0. A 10% w/v solution of sodium caseinate was prepared and adjusted to pH 8.0. Trypsin (Novo) was added to 0.2% w/v and the hydrolysis allowed to proceed to completion at 37° C. with adjustment to pH 8.0 by constant addition of NaOH. The pH of the solution was then adjusted to pH 4.7 with 5M HCl and the precipitate removed at room temperature by centrifugation. The supernatant was adjusted to pH 7.0 with NaOH and CaCl$_2$ added to a level of 1.0% w/v. This solution was then diafiltered through an Amicon YM10 (10,000 molecular weight exclusion limit) with 5 volumes of 1.0% w/v CaCl$_2$. The retentate was then washed with 1 volume of distilled/deionised water through an Amicon YM1 filter (1,000 molecular weight exclusion limit). The individual peptides of this preparation were separated by ion exchange FPLC and reverse phase HPLC as described in our U.S. Pat. No. 5,015,628 and identified by amino acid composition and sequence analyses after conversion of the Ser(P) residues to S-ethyl cysteine.

The calcium salt of the casein phosphopeptide preparation (CPP) produced by the above method can be converted to a sodium salt by acidifying a 10% w/v solution of the calcium CPP to a low pH, circa pH 2.0, with HCl. After extensive disfiltration through a 1,000 molecular weight exclusion limit filter the retentate is neutralised to pH 7.0 with NaOH and then disfiltered with water through the same filter to remove excess sodium chloride.

A typical ZnCPP ultrafiltration preparation from a tryptic digest of commercial caseinate contains SEQ.ID NO:1, 22.3% w/w; SEQ.ID NO:2, 21.4% w/w; SEQ.ID NO:3, 17.9% w/w; SEQ.ID NO:4, 6.8% w/w; SEQ.ID NO:5, 6.3% w/w; SEQ.ID NO:6, 6.4% w/w; SEQ.ID NO:7, 5.7% w/w; SEQ.ID NO:8, 0.8%; SEQ.ID NO:9, 3.3% w/w and non-active peptides 9.1% w/w. It is important to note that more severe hydrolysis conditions (e.g. high temperatures, extremes of pH and "non-trypsin-like" protesses) will result in deamidated and/or dephosphorylated and/or shorter or longer peptides than detailed in the "Sequence Listing". These shorter, longer and/or deamidated peptides will still have anticalculus activity if they contain the sequence -Glu-Ser(P)-Ile/Leu-Ser(P)-Ser(P)-Ser(P)-Glu-Glu- or to a lesser extent -Ser(P)-Ser(P)-Ser(P)-Glu-Glu. It is preferred, however, to control the hydrolysis to minimize breakdown of the CPP and therefore maximize anticalculus activity.

The CPP may be used as such, or in the form of their alkali metal, alkaline earth metal or transition metal salts. Typical examples are sodium salts, calcium salts, zinc, copper, aluminium, potassium, strontium, magnesium and nickel salts. Sodium and zinc salts are most preferred. Accordingly, it is contemplated that the present invention is not limited to specific salts mentioned herein and that other cationic metal salts of the CPP particularly cationic transition metal salts could be formed and used for the purposes described herein. It is also possible and within the scope of the present invention to have physical combinations of compounds of the prior art (e.g. pyrophosphates) which are known to inhibit dental calculus and one or more of the CPP. Such compositions may exert a synergistic or additive effect in terms of dental calculus inhibition.

The method of the present invention involves applying to the teeth a composition comprising specific CPP. Such a composition usually contains from about 0.01 to about 30% by weight of the CPP preferably from about 0.1 to 10% and most preferably 1.0 to 5.0%. Such compositions may be an aqueous, aqueous-alcohol or alcohol solution or dispersion of the CPP in the form of a mouthwash, dentifrice, toothpaste, toothpowder, gel, lozenge, tablet, chewing gum, foodstuff or drink, or any other suitable form of an oral composition. The pH or these preparations should be between 2 and 10. Extremes of pH will dephosphorylate and therefore inactivate the CPP. Preferably the pH should be between 5 and 9.

Dental calculus inhibitory activity of the CPP can be destroyed by dephosphorylation of the phosphoserines via the action of intra-oral plaque bacterial phosphatase activity. It is desirable, therefore, to stabilize the CPP against phosphatase and peptidase activity. Examples of phosphatase inhibitors to be used in conjunction with the CPP to prevent or inhibit dephosphorylation are fluoride ions, vinyl ether maleic acid polymers (gantrez) and aggregating divalent and trivalent metal ions (e.g. Zn(II)). Zinc ions aggregate the CPP producing a zinc CPP complex with approximately 6 moles of zinc ions per mole CPP. This aggregate or complex of zinc and CPP is referred to as ZnCPP. ZnCPP has been shown to be stabilized against intra-oral phosphatase and peptidase activity and also has been shown to have an increased oral retention when compared with NaCPP, an enhanced incorporation into dental plaque and enhanced potential anti-calculus activity.

CPP stabilize calcium phosphate, specifically they bind to spontaneously forming clusters of amorphous calcium phosphate and retard or prevent phase transition into the crystalline forms, in particular, hydroxyapatite. Further, CPP bind to crystalline phases of calcium phosphate and retard or prevent crystal growth. The CPP also stabilise the more acidic forms of calcium phosphate e.g. Brushite (CaHPO$_4$.2H$_2$O) and retard or prevent transformation into the more basic forms, in particular hydroxyapatite. Using synthetic peptides the active centre of the CPP has been identified as the sequence -Glu-Ser(P)-Ile/Leu-Ser(P)-Ser(P)-Ser(P)-Glu-Glu- and to a lesser extent the pentamer -Ser(P)-Ser(P)-Ser(P)-Glu-Glu-. However, it should be noted that the specific activity of the synthetic octamer above was only half that of the CPP SEQ.ID NO:1 and SEQ.ID NO:2 on a molar basis. This clearly indicates that other amino acyl residues of the CPP are important for full activity.

The preferred oral compositions of the present invention are in the form of toothpaste creams or gels, or mouthwashes. Ingredients typically included in toothpaste and gels may be used in toothpaste and gel compositions in accordance with the invention. Suitable ingredients include abrasive polishing materials, sudsing agents, flavoring agents, humectants, binders, sweetening agents, and water. Abrasives which may be used in the compositions of the invention include alumina and hydrates thereof, such as alpha alumina trihydrate, magnesium trisilicate, magnesium carbonate, aluminosilicate, such as calcined aluminium silicate and aluminium silicate, calcium carbonate, zirconium silicate, polymethylmethacrylate, powdered polyethylene, silica xerogels, hydrogels and aerogels and the like. Also suitable as abrasive agents are calcium pryophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (NATROSO®, and hydroxypropyl cellulose (KLUCEI®), as well as xanthan gums, Iris moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Surfactants, such as a soap, anionic, nonionic, cationic, amphoteric and/or zwitterionic, may be present within the range of 0 to 15%, preferably 0.1 to 15%, more preferably 0.25 to 10% by weight. Anionic surfactants are most preferred, such as sodium dodecyl sulfate, sodium lauryl sarcosinate and sodium dodecylbenzene sulfonate. Flavors are usually included in toothpastes in low amounts, such as from 0.01 to about 5% by weight, especially from 0.1% to 5%.

Ingredients mentioned above as suitable for toothpastes are generally suitable for gels, as will be apparent to one skilled in the art of toothpaste and gel formulation. Thus, except where otherwise noted, references to toothpastes are to be construed as applying to gels as well. Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 60%, preferably from 5 to 30% by weight.

Antibacterial agents, for example phenolics such as Irgasan DP300 (ex Ciba-Geigy) and salicylamides (including salicylanilides), and sources of certain metal ions such as zinc, copper, silver and stannous (e.g. zinc, copper and stannous chloride, and silver nitrate) may also be, and preferably are included. Dyes/colorants suitable for dentifrices, i.e. FD & C Blue #1, FD & C Yellow #10, FD & C Red #40, etc., may be employed in the dentifrices of the invention. Various other optional ingredients may be included in the compositions of the invention, such as preservatives, vitamins such as vitamin C and E, other anti-plaque agents such as stannous salts, copper salts, strontium salts and magnesium salts. Also included may be pH adjusting agents, anti-caries agents such as urea, calcium glycerophosphate, sodium trimetaphosphate, anti-staining compounds such as silicone polymers, plant extracts, desensitizing agents for sensitive teeth such as potassium nitrate and potassium citrate, and mixtures thereof. Additionally, polymers, particularly anionic polymers, such as polycarboxylates or polysulfonates, or polymers containing both a carboxylate and a sulfonate moiety may be included.

EXAMPLE 1

Comparative in vitro experiments were performed using an established model of calculus inhibition the Seeded Crystal Growth Inhibition Assay. From a typical experiment the inhibition of seeded hydroxyapatite (HA) crystal growth by CPP and synthetic peptides is presented in the following table. The composition of the experimental solutions was 1.06 mmol/L in $CaCl_2$ and 0.63 mmol/L in inorganic phosphate (Pi). The pH was adjusted to 7.40 by the appropriate combination of $H_2PO_4^-$ and $HPO_4^{2-}$, and the ionic strength was controlled by the addition of NaCl. The HA used as seeds had a specific surface area of 16.3 $m^2/g$ and a Ca/P molar ratio of 1.66 and was prior incubated with the respective peptide solution or control solution. The control solution was the same pH and ionic strength but was minus the peptide. At time zero, HA seeds (25 mg) were added to the thermostated solution (37° C.±0.5° C.) and the change in solution composition with time (due to crystal growth) was monitored by pH and by withdrawing small samples of suspension. The samples were filtered to remove the HA crystals and the filtrate analysed for Pi. The inhibition of seeded crystal growth was expressed as $[\Delta_{[Pi]}\text{control} - \Delta_{[Pi]}\text{peptide}]/\Delta_{[Pi]}\text{control} \times 100$.

| Inhibition of Hydroxyapatite Seeded Crystal Growth | | |
|---|---|---|
| Peptide | Coating Concentration μmol/L | Inhibition* % |
| NaCPP | 50 | 61 |
| ZnCPP | 50 | 82 |
| SEQ. ID NO: 1/Na | 50 | 62 |
| SEQ. ID NO: 2/Na | 50 | 61 |
| EΣIΣΣΣEE§ | 50 | 31 |
| EΣLΣΣΣEE | 50 | 30 |
| ΣΣΣEE | 50 | 22 |
| IVPNΣVEQ | 50 | 5 |
| QMEAE | 50 | 0 |

*% Inhibition = $[\Delta_{[Pi]}\text{control} - \Delta_{[Pi]}\text{peptide}]/\Delta_{[Pi]}\text{control} \times 100$.
§Synthetic peptides where Σ is phosphoserine, E is glutamate, I is isoleucine, L is leucine, V is valine, P is proline, N is asparagine, Q is glutamine, M is methionine, A is alanine.

EXAMPLE 2

Peptide bound calcium phosphate was determined using the ultrafiltration method. The peptides at 0.1–2.0 mM in 100 mM Tris/CHES (pH 7.0, 8.0, 9.0) 0 or 12 mM $CaCl_2$ and sodium phosphate ranging from 0 to 8.0 mM (NaCl was added to give a constant ionic strength 0.15) were left to equilibrate 18 h at 37° C. Solutions with precipitate were discarded. Less than 10% v/v of the solution was then passed through an Amicon micropartition cell equiped with a 1000 $M_r$ exclusion limit filter. Calcium and phosphate concentrations in the original solution (to confirm no precipitation) and the ultrafiltrate were determined using AAS and colorimetry respectively. Peptide-bound calcium phosphate were determined by the difference in the total and free calcium and phosphate respectively. The binding of calcium phosphate was expressed as a function of the ion activity product of the various calcium phosphates to determine the function which was independent of pH. The ion activity products for the various phases of calcium phosphate were determined from the free calcium and phosphate concentrations and pH using a modified computer programme that calculates the ion activity coefficients through the use of the expanded Debye-Huckel equation and takes into account ion pairs $CaHPO_4°$, $CaH_2PO_4^+$, $CaPO_4^-$, $CaOH^+$, the dissociation of $H_3PO_4$ and $H_2O$ and the ionic strength. The binding of calcium phosphate by the CPP and synthetic peptides is shown in the following table.

| Calcium Phosphate Binding by CPP and Synthetic Peptides | | | |
|---|---|---|---|
| Peptide | pH | $v_{ca}$ mol/mol | $v_{Pi}$ mol/mol |
| SEQ. ID NO: 1 | 9.0 | 24 | 17 |
| SEQ. ID NO: 2 | 9.0 | 24 | 17 |
| EΣIΣΣΣEE§ | 9.0 | 12 | 7 |
| EΣLΣΣΣEE | 9.0 | 12 | 7 |
| ΣΣΣEE | 9.0 | 9 | 5 |
| AΣAΣAΣAE | 9.0 | 2 | 1 |
| IVPNΣVEQ | 9.0 | 0 | 0 |
| QMEAE | 9.0 | 0 | 0 |
| AΣAE | 9.0 | 0 | 0 |
| AΣAΣAE | 9.0 | 0 | 0 |

§Synthetic peptides where Σ is phosphoserine, E is glutamate, I is isoleucine, L is leucine, V is valine, P is proline, N is asparagine, Q is glutamine, M is methionine, A is alanine.

The calcium phosphate bound and stabilized by the peptides was shown to be amorphous calcium phosphate [$Ca_{1.5}(PO_4)$].

EXAMPLE 3

Comparative experiments were performed using the CPP and synthetic peptides in the Seeded Crystal Growth Assay using Brushite (dicalcium phosphate dihydrate, DCPD) as the crystalline phase. The supersaturated solution used in the crystal growth experiments with DCPD had the following composition, Ca and Pi 5.3 mmol/L, pH 6.10, 50 mmol/L NaCl. Each peptide was added to the supersaturated solution at a concentration of 1.0 μmol/L. The DCPD used as seeds had a molar ratio of 0.99 and a specific surface area of 1.12 $m^2/g$. At time zero DCPD was added to the solution and at various times assayed for Pi after removal of the crystalline phase. The effect of CPP and synthetic peptides is shown in the following table.

| Inhibition of Brushite [$CaHPO_4.2H_2O$] Seeded Crystal Growth. | |
|---|---|
| Peptide | Inhibition* (%) |
| NaCPP | 85 |
| ZnCPP | 97 |
| EΣIΣΣΣEE§ | 53 |
| EΣLΣΣΣEE | 52 |
| ΣΣΣEE | 31 |
| IVPNΣEQ | 5 |
| QMEAE | 0 |

§Synthetic peptides where Σ is phosphoserine, E is glutamite, I is isoleucine, L is leucine, V is valine, P is proline, N is asparagine, Q is glutamine, M is methionine, A is alanine.
*% Inhibition = [$\Delta_{[Pi]}$control − $\Delta_{[Pi]}$peptide]/$\Delta_{[Pi]}$control × 100

EXAMPLE 4

The binding of zinc ions to CPP was determined using the same experimental technique as described in Example 2 for calcium phosphate binding. A NaCPP solution 10 mg/ml containing 20 mmol/L $ZnSO_4$ at pH 6.7 was ultrafiltered through a 1,000 MW exclusion limit filter and the ultrafiltrate analysed by atomic absorption spectrophotometry. The ultrafiltrate contained 1 mmol/L free zinc ions indicating that 19 mmol/L was bound which represents 6 $Zn^{2+}$ per CPP molecule of the aggregate. The size of the ZnCPP aggregate suggested at least six CPP molecules per complex.

EXAMPLE 5

The incorporation of NaCPP and ZnCPP into dental plaque was determined using the peptides in a mouthwash at 3 mmol/L. The mouthwash was used twice daily by individuals who abstained from oral hygiene for 3 days. On the fourth day supragingival plaque from the lower anterior teeth was collected and analysed for CPP using specific antibodies in a quantitative competitive ELISA. The CPP level in plaque after the NaCPP mouthwash was 107±51 μg/g plaque. However, the CPP level in plaque after the ZnCPP mouthwash was 266±65 μg/g which was significantly ($P<0.05$) higher.

EXAMPLE 6

Typical formulation for a mouthwash, containing the CPP according to the invention, is as follows:

| Mouthwash Formulation | | |
|---|---|---|
| | % by weight of final composition | |
| Ingredients | A | B |
| Ethanol | 12.5 | 12.5 |
| 70% Sorbitol | 7 | 7 |
| NaCPP | — | 5 |
| Tween 20 | 0.55 | 0.55 |
| Preservatives* | 0.2 | 0.2 |
| Flavor | 0.1 | 0.1 |
| ZnCPP | 5 | — |
| Dye | <0.01 | <0.01 |
| Sodium Saccharinate | 0.065 | 0.065 |
| Sodium chloride | 0.05 | 0.05 |
| Na acetate | 0.015 | 0.015 |
| Acetic acid | 0.015 | 0.015 |
| $H_2O$ | to 100 | to 100 |
| pH | 6.5 | 6.5 |

*0.1% methylparaben

EXAMPLE 7

Typical toothpaste formulations, containing CPP according to the invention, are as follows:

| Toothpaste Formulations pH 6-9 | | | | |
|---|---|---|---|---|
| | Final Composition (% w/w) | | | |
| | A | B | C | D |
| 70% Sorbitol | 64 | 39 | 64 | 39 |
| Abrasive silica | 10 | 10 | 10 | 10 |
| Thickening silica | 9 | 10 | 9 | 10 |
| NaCPP | — | — | 5 | 5 |
| Polyethylene glycol (PEG 32 ®) | 5 | 5 | 5 | 5 |
| ZnCPP | 5 | 5 | — | — |
| Sodium Lauryl Sulfate | 1.5 | 1.5 | 1.5 | 1.5 |
| Flavor | 1 | 1 | 1 | 1 |
| Sodium saccharinate | 0.3 | 0.2 | 0.3 | 0.2 |
| Na Fluoride | 0.24 | 0.24 | 0.24 | 0.24 |
| Preservative (Na Benzoate) | 0.08 | 0.08 | 0.08 | 0.08 |
| Dye | <0.01 | — | <0.01 | — |
| Titanium oxide | — | 1 | — | 1 |
| Xanthan Gum | 0.15 | 0.6 | 0.15 | 0.6 |
| $H_2O$ | to 100 | to 100 | to 100 | to 100 |

I claim:

1. A method of inhibiting dental calculus in an animal having teeth comprising applying to the teeth an oral composition containing a dental calculus inhibiting amount of one or more phosphopeptides containing 5 to 40 amino acyl residues and include the sequence -Ser(P)-Ser-(P)-Ser(P)-Glu-Glu where Ser(P) is phosphoserine and Glu is glutamate, or salts thereof.

2. The method of claim 1, wherein the phosphopeptides include the sequence-Glu-Ser(P)-Ile/Leu-Ser(P)-Ser(P)-Ser(P)-Glu-Glu-whereIle is isoleucine and Leu is leucine.

3. The method of claim 1, wherein the phosphopeptides are selected from the group consisting of the sequences Arg—Glu—Leu—Glu—Glu—Leu—Asn—Val—Pro—Gly—Glu—Ile—Val—Glu—Ser—Leu—
Ser—Ser—Ser—Glu—Glu—Ser—Ile—Thr—Arg,
Gln—Met—Glu—Ala—Glu—Ser—Ile—Ser—Ser—Ser—Glu—Glu—Ile—Val—Pro—Asn—
Ser—Val—Glu—Gln—Lys,
Glu—Leu—Glu—Glu—Leu—Asn—Val—Pro—Gly—Glu—Ile—Val—Glu—Ser—Leu—Ser—
Ser—Ser—Glu—Glu—Ser—Ile—Thr—Arg,
Asn—Ala—Asn—Glu—Glu—Glu—Tyr—Ser—Ile—Gly—Ser—Ser—Ser—Glu—Glu—Ser—
Ala—Glu—Val—Ala—Thr—Glu—Glu—Val—Lys,
Gln—Met—Glu—Ala—Glu—Ser—Ile—Ser—Ser—Ser—Glu—Glu—Ile—Val—Pro—Asp—
Ser—Val—Glu—Gln—Lys,
Gln—Met—Glu—Ala—Glu—Ser—Ile—Ser—Ser—Ser—Glu—Glu—Ile—Val—Pro—Asp—
Ser—Val—Glu—Glu—Lys,
Asn—Thr—Met—Glu—His—Val—Ser—Ser—Ser—Glu—Glu—Ser—Ile—Ile—Ser—Gln—
Glu—Thr—Tyr—Lys,
Lys—Asn—Thr—Met—Glu—His—Val—Ser—Ser—Ser—Glu—Glu—Ser—Ile—Ile—Ser—
Gln—Glu—Thr—Tyr—Lys,
Asp—Ile—Gly—Ser—Glu—Ser—Thr—Glu—Asp—Gln—Ala—Met—Glu—Asp—Ile—Lys—
Gln—Met—Glu—Ala—Glu—Ser—Ile—Ser—Ser—Ser—Glu—Glu—Ile—Val—Pro—Asn, or mixtures thereof.

4. The method of claim 1, wherein said phosphopeptides are in the form of salts selected from alkaline metal, alkaline earth metal or transition metal salts such as sodium, calcium, zinc, copper, aluminium, potassium, strontium, magnesium and nickel salts.

5. The method of claim 1, wherein said phosphopeptides are in the form of divalent or trivalent metal ion complexes or aggregates.

6. The method of claim 1, wherein said oral composition contains a phosphatase inhibitor selected from fluoride ions, vinyl ether maleic acid polymers (gantrez) and aggregating divalent and trivalent metal ions.

7. An oral composition comprising a dental calculus inhibiting amount of one or more phosphopeptides containing from 5 to 40 amino acyl residues and include the sequence -Ser(P)-Ser(P)-Ser(P)-Glu-Glu where Ser(P) is phosphoserine and Glu is glutamate, or salts thereof in a pharmaceutically acceptable carrier.

8. The composition of claim 7, wherein said composition also contains an effective amount of a phosphatase inhibitor selected from fluoride ions, vinyl ether maleic acid polymers (gantrez) and aggregating divalent and trivalent metal ions.

9. An oral composition comprising a dental calculus inhibiting amount of one or more phosphopeptides containing 5 to 40 amino acyl residues and include the sequence -Ser(P)-Ser(P)-Ser(P)-Glu-Glu where Ser(P) is phosphoserine and Glu is glutamate, or salts thereof present as a divalent or trivalent metal ion complex or aggregate.

10. The composition of claim 9, wherein said phosphopeptides further contain the sequence -Glu-Ser(P)-Ile/Leu-Ser(P)-Ser(P)-Ser(P)-Glu-Glu-where Ile is isoleucine and Leu is leucine.

11. The composition of claim 9, wherein said phosphopeptides are selected from the group consisting of the sequences Arg—Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg.
Gln—Met—Glu—Ala—Glu—Ser—Ile—Ser—Ser—Ser—Glu—Glu—Ile—Val—Pro—Asn—Ser—Val—Glu—Gln—Lys,
Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg,
Asn—Ala—Asn—Glu—Glu—Glu—Tyr—Ser—Ile—Gly—Ser—Ser—Ser—Glu—Glu—Ser—Ala—Glu—Val—Ala—Thr—Glu—Glu—Val—Lys,
Gln—Met—Glu—Ala—Glu—Ser—Ile—Ser—Ser—Ser—Glu—Glu—Ile—Val—Pro—Asp—Ser—Val—Glu—Gln—Lys,
Gln—Met—Glu—Ala—Glu—Ser—Ile—Ser—Ser—Ser—Glu—Glu—Ile—Val—Pro—Asp—Ser—Val—Glu—Glu—Lys,
Asn—Thr—Met—Glu—His—Val—Ser—Ser—Ser—Glu—Glu—Ser—Ile—Ile—Ser—Gln—Glu—Thr—Tyr—Lys,
Lys—Asn—Thr—Met—Glu—His—Val—Ser—Ser—Ser—Glu—Glu—Ser—Ile—Ile—Ser—Gln—Glu—Thr—Tyr—Lys,
Asp—Ile—Gly—Ser—Glu—Ser—Thr—Glu—Asp—Gln—Ala—Met—Glu—Asp—Ile—Lys—
Gln—Met—Glu—Ala—Glu—Ser—Ile—Ser—Ser—Ser—Glu—Glu—Ile—Val—Pro—Asn, or mixtures thereof.

12. The oral composition of claim 9, wherein the phosphopeptides are present as a zinc/phosphopeptide complex or aggregate.

13. The method of claim 2, wherein the phosphopeptides are selected from the group consisting of the sequences Arg—Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg,
Gln—Met—Glu—Ala—Glu—Ser—Ile—Ser—Ser—Ser—Glu—Glu—Ile—Val—Pro—Asn—Ser—Val—Glu—Gln—Lys,
Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg,
Asn—Ala—Asn—Glu—Glu—Glu—Tyr—Ser—Ile—Gly—Ser—Ser—Ser—Glu—Glu—Ser—Ala—Glu—Val—Ala—Thr—Glu—Glu—Val—Lys,
Gln—Met—Glu—Ala—Glu—Ser—Ile—Ser—Ser—Ser—Glu—Glu—Ile—Val—Pro—Asp—Ser—Val—Glu—Gln—Lys,
Gln—Met—Glu—Ala—Glu—Ser—Ile—Ser—Ser—Ser—Glu—Glu—Ile—Val—Pro—Asp—Ser—Val—Glu—Glu—Lys,
Asn—Thr—Met—Glu—His—Val—Ser—Ser—Ser—Glu—Glu—Ser—Ile—Ile—Ser—Gln—Glu—Thr—Tyr—Lys,
Lys—Asn—Thr—Met—Glu—His—Val—Ser—Ser—Ser—Glu—Glu—Ser—Ile—Ile—Ser—Gln—Glu—Thr—Tyr—Lys,
Asp—Ile—Gly—Ser—Glu—Ser—Thr—Glu—Asp—Gln—Ala—Met—Glu—Asp—Ile—Lys—
Gln—Met—Glu—Ala—Glu—Ser—Ile—Ser—Ser—Ser—Glu—Glu—Ile—Val—Pro—Asn, or mixtures thereof.

14. The method of claim 2, wherein said phosphopeptides are in the form of salts selected from alkaline metal, alkaline earth metal or transition metal salts such as sodium, calcium, zinc, copper, aluminum, potassium, strontium, magnesium and nickel salts.

15. The method of claim 3, wherein said phosphopeptides are in the form of salts selected from alkaline metal, alkaline earth metal or transition metal salts such as sodium, calcium, zinc, copper, aluminum, potassium, strontium, magnesium and nickel salts.

16. The method of claim 2, wherein said phosphopeptides are in the form of divalent or trivalent metal ion complexes or aggregates.

17. The method of claim 3, wherein said phosphopeptides are in the form of divalent or trivalent metal ion complexes or aggregates.

18. The method of claim 2, wherein said oral composition contains a phosphatase inhibitor selected from fluoride ions, vinyl ether maleic acid polymers (gantrez) and aggregating divalent and trivalent metal ions.

19. The method of claim 3, wherein said oral composition contains a phosphatase inhibitor selected from fluoride ions, vinyl ether maleic acid polymers (gantrez) and aggregating divalent and trivalent metal ions.

20. The composition of claim 10, wherein said phosphopeptides are selected from the group consisting of the sequences Arg—Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg,
Gln—Met—Glu—Ala—Glu—Ser—Ile—Ser—Ser—Ser—Glu—Glu—Ile—Val—Pro—Asn—Ser—Val—Glu—Gln—Lys,
Glu—Leu—Glu—Glu—Leu—Asn—Val—Pro—Gly—Glu—Ile—Val—Glu—Ser—Leu—Ser—Ser—Ser—Glu—Glu—Ser—Ile—Thr—Arg,
Asn—Ala—Asn—Glu—Glu—Glu—Tyr—Ser—Ile—Gly—Ser—Ser—Ser—Glu—Glu—Ser—Ala—Glu—Val—Ala—Thr—Glu—Glu—Val—Lys,
Gln—Met—Glu—Ala—Glu—Ser—Ile—Ser—Ser—Ser—Glu—Glu—Ile—Val—Pro—Asp—Ser—Val—Glu—Gln—Lys,
Gln—Met—Glu—Ala—Glu—Ser—Ile—Ser—Ser—Ser—Glu—Glu—Ile—Val—Pro—Asp—Ser—Val—Glu—Glu—Lys,
Asn—Thr—Met—Glu—His—Val—Ser—Ser—Ser—Glu—Glu—Ser—Ile—Ile—Ser—Gln—Glu—Thr—Tyr—Lys,
Lys—Asn—Thr—Met—Glu—His—Val—Ser—Ser—Ser—Glu—Glu—Ser—Ile—Ile—Ser—Gln—Glu—Thr—Tyr—Lys,
Asp—Ile—Gly—Ser—Glu—Ser—Thr—Glu—Asp—Gln—Ala—Met—Glu—Asp—Ile—Lys—

-continued

Gln—Met—Glu—Ala—Glu—Ser—Ile—Ser—Ser—Ser—Glu—Glu—Ile—Val—Pro—Asn, or mixtures thereof.

21. The oral composition of claim 10, wherein the phosphopeptides are present as a zinc/phosphopeptide complex or aggregate.

22. The oral composition of claim 11, wherein the phosphopeptides are present as a zinc/phosphopeptide complex or aggregate.

* * * * *

UNITED STATES PATENT AND TRADEMARK OFFICE
CERTIFICATE OF CORRECTION

PATENT NO. : 5,227,154
DATED : July 13, 1993
INVENTOR(S) : Eric C. Reynolds

It is certified that error appears in the above-indentified patent and that said Letters Patent is hereby corrected as shown below:

On the Title Page, Item [73]:

After "The University of Melbourne, Australia" insert ---and Victorian Dairy Industry Authority, Australia---

Signed and Sealed this

Nineteenth Day of April, 1994

Attest:

BRUCE LEHMAN

*Attesting Officer*    *Commissioner of Patents and Trademarks*